United States Patent
Fukushima et al.

(10) Patent No.: US 9,254,117 B2
(45) Date of Patent: Feb. 9, 2016

(54) ULTRASONIC ENDOSCOPIC PROBE

(71) Applicant: NAMIKI SEIMITSU HOUSEKI KABUSHIKI KAISHA, Tokyo (JP)

(72) Inventors: Eri Fukushima, Kuroishi (JP); Hiroshi Yamazaki, Kuroishi (JP); Takafumi Asada, Kuroishi (JP)

(73) Assignee: Namiki Seimitsu Houseki Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/473,924

(22) Filed: Aug. 29, 2014

(65) Prior Publication Data

US 2015/0065884 A1 Mar. 5, 2015

(30) Foreign Application Priority Data

Aug. 31, 2013 (JP) .................. 2013-180771

(51) Int. Cl.
 *A61B 8/00* (2006.01)
 *A61B 8/12* (2006.01)
(52) U.S. Cl.
 CPC . *A61B 8/445* (2013.01); *A61B 8/12* (2013.01); *A61B 8/4461* (2013.01)
(58) Field of Classification Search
 CPC ........ A61B 8/4281; A61B 8/445; A61B 8/12; A61B 8/14; A61B 8/4461; A61B 8/483
 See application file for complete search history.

(56) References Cited

U.S. PATENT DOCUMENTS

| | | | |
|---|---|---|---|
| 2008/0097403 A1 | 4/2008 | Donaldson et al. | |
| 2010/0145310 A1 | 6/2010 | Lee et al. | |
| 2010/0256502 A1 | 10/2010 | Buckley et al. | |

FOREIGN PATENT DOCUMENTS

| | | |
|---|---|---|
| JP | 05-228149 A | 9/1993 |
| JP | 07-289550 A | 11/1995 |
| JP | 11-113921 A | 4/1999 |
| JP | 2000-166157 A | 6/2000 |
| JP | 2002-142406 A | 5/2002 |
| JP | 2004-261359 A | 9/2004 |
| JP | 2008-272445 A | 11/2008 |
| JP | 2009-285322 A | 12/2009 |
| JP | 2010-131387 A | 6/2010 |
| JP | 2010-240424 A | 10/2010 |
| WO | 2014/115360 A1 | 7/2014 |
| WO | 2014/115361 A1 | 7/2014 |

*Primary Examiner* — Joel Lamprecht
(74) *Attorney, Agent, or Firm* — Studebaker & Brackett PC

(57) ABSTRACT

Provided is an ultrasonic endoscopic probe capable of obtaining an ultrasonic observation image having high spatial resolution. A part of a substantially tubular catheter is sealed with seal plates to provide a cavity housing: a motor including a motor casing, a rotor magnet, a bearing, and a rotating shaft; an ultrasonic transducer mounted to the rotating shaft; and a signal transmission means. The bearing includes an inner peripheral surface provided with a plurality of dynamic pressure generating grooves. An acoustic coupling fluid is sealed in the cavity and is allowed to penetrate a gap between the bearing and the rotating shaft at all times. When the ultrasonic transducer and the motor are rotated in the acoustic coupling fluid, the acoustic coupling fluid is suctioned in a preferable manner into the bearing gap having the dynamic pressure generating grooves for lubrication. Thus, a lack of an oil film on the bearing can be prevented, allowing for high accuracy rotation. Operational failure due to the development of foam in the acoustic coupling fluid can be prevented, enabling the acquisition of a high resolution ultrasonic observation image.

6 Claims, 8 Drawing Sheets

FIG. 6

| Acoustic Coupling Fluid | Bubble | Oil Film |
|---|---|---|
| Mineral Oil | ○ | ○ |
| Silicon Oil | ○ | ○ |
| Flourine Oil | △ | ○ |
| Water | ○ | × |

ULTRASONIC ENDOSCOPIC PROBE

CROSS-REFERENCE TO RELATED APPLICATION

This application claims priority from Japanese Patent Application No. 2013-180771 filed with the Japan Patent Office on Aug. 31, 2013, the entire content of which is hereby incorporated by reference.

BACKGROUND

1. Technical Field

The present invention relates to ultrasonic endoscopic probes in medical equipment and the like for acquiring, for observation, ultrasonic waves reflected by a tested specimen irradiated with ultrasonic waves radiated from an ultrasonic transducer rotated by a motor built inside the tip of the probe.

2. Related Art

Diagnostic imaging technology is widely utilized in the fields of analysis, medicine and the like. For example, in the medical or precision device manufacturing field, various diagnostic imaging techniques are being researched and utilized, in addition to the conventional observations using cameras. Examples of such diagnostic imaging technologies include X-ray CT and nuclear magnetic resonance systems that enable tomographic imaging, ultrasonic diagnostic devices that capture ultrasonic reflections, and optical coherence tomography systems utilizing the coherence of light. One of the tomographic imaging systems that have been most extensively utilized in recent years is the ultrasonic diagnostic device characterized by its relatively deep scan depth.

An ultrasonic transducer used in the ultrasonic diagnostic device has an oscillation frequency of the order of 10 to 20 MHz in conventional devices, with the wavelength of several tens of μm. Thus, compared with the optical coherence tomography system in which the light source uses near-infrared light with the wavelength of 1.3 micron, the ultrasonic diagnostic device is disadvantageous in that the spatial resolution required of a diagnostic device is not easily achievable due to the longer wavelength. However, it has become possible in recent years to increase the oscillation frequency of the ultrasonic transducer up to 300 MHz or above, with the wavelength having been improved to the level comparable to that of near-infrared light used in optical coherence tomography. Ultrasonic diagnosis is non-invasive to living bodies and is now capable of identifying objects with the spatial resolution of approximately 10 μm (microns). Thus, there are expectations that, particularly in the medical field, the ultrasonic diagnostic device can be built inside the thin tip portion of an endoscope and utilized for the discovery, diagnosis, or treatment of an affected area in the stomach, the small intestine, the arterial vessels and the like of the human body. Representative structures of the ultrasonic endoscope in which the ultrasonic diagnostic imaging technology is applied are discussed in JP-A-2010-131387 and U.S. Pat. No. 8,211,025 B2, for example.

In the ultrasonic endoscope described in JP-A-2010-131387, as shown in FIG. 2 of the literature, an output drive shaft 51 of a micromotor 41 is provided with a barrier membrane film seal 60 for isolating an acoustic coupling fluid 29, which entirely covers a transducer 53, from the micromotor 41, thus preventing the entry of the acoustic coupling fluid 29 into the micromotor 41. From the transducer, ultrasonic waves are radiated onto the tested specimen, and a reflected ultrasonic waveform is captured by the transducer, enabling the observation of the state of the tested specimen.

However, as the micromotor 41 starts rotation, the internal air expands as the temperature increases, and the air may enter via a gap of the barrier membrane film seal 60 into the acoustic coupling fluid 29, producing air bubbles therein. In the ultrasonic endoscope, the air bubbles in the acoustic coupling fluid 29 would reflect the ultrasonic waves radiated from the transducer, preventing the ultrasonic waves from reaching the tested portion located further ahead and interfering with observation.

In U.S. Pat. No. 8,211,025 B2, as shown in FIG. 3 of the literature, a gear box and a motor 320 are disposed in a fluid-filled portion of a catheter body 360 filled with acoustic coupling fluid. A shaft 340 of the motor 320 causes an ultrasonic transducer 310 to rotate in an oscillatory manner at certain angles. From the transducer 310, ultrasonic waves are radiated toward the tested specimen, and a reflected ultrasonic waveform is captured by the transducer 310 to observe the state of the tested specimen.

In this structure, lubrication oil or grease previously injected into the motor bearings may dissolve into the acoustic coupling fluid, degrading the transmission characteristics of the acoustic coupling fluid. Further, the antifoaming performance of the acoustic coupling fluid may be hampered by chemical reaction, producing air bubbles and interfering with observation of the tested portion. In addition, lubrication of the motor bearings may be adversely affected, causing frictions in the bearings and producing uneven rotation speed or an increase in the amount of oscillation. As a result, the transducer 310 may become unable to sufficiently transmit or receive ultrasonic waves, resulting in deterioration in the observed image or preventing the acquisition of the spatial resolution required by the ultrasonic endoscope.

SUMMARY

The present invention was made in view of the above circumstances, and is aimed at solving the problem of providing an ultrasonic endoscopic probe in which an ultrasonic transducer is rotated together with a motor in an acoustic coupling fluid, the probe being capable of preventing operation failure due to a lack of an oil film on bearings caused by the mixing of bearing oil with the acoustic coupling fluid, or due to the development of foam, and being capable of producing an observation image having high spatial resolution enabled by high accuracy rotation.

A means for solving the problem comprises a substantially tubular catheter including a cavity formed by sealing a part of the catheter with a seal plate. The cavity houses a motor including a motor casing, a bearing, and a rotating shaft to which an ultrasonic transducer is mounted, and a signal transmission means for transmitting or receiving a signal to or from the ultrasonic transducer. The motor bearing includes an inner peripheral surface provided with a plurality of dynamic pressure generating grooves parallel with an axial direction. An acoustic coupling fluid is sealed in the cavity. The bearing provided with the dynamic pressure generating grooves has a gap configured to suction the acoustic coupling fluid for lubricating the bearing.

According to the present invention, when the ultrasonic transducer and the motor are rotated in the acoustic coupling fluid, the acoustic coupling fluid is suctioned into the bearing gap, thus lubricating the bearing. Accordingly, operational failure due to the lack of an oil film on the bearing or the development of foam can be prevented, whereby highly accurate rotation can be executed and a high resolution observation image can be obtained.

BRIEF DESCRIPTION OF DRAWINGS

FIG. 6 is a chart for describing the characteristics of the acoustic coupling fluid of the ultrasonic endoscopic probe according to the first embodiment of the present invention;

DETAILED DESCRIPTION

Figure 1:
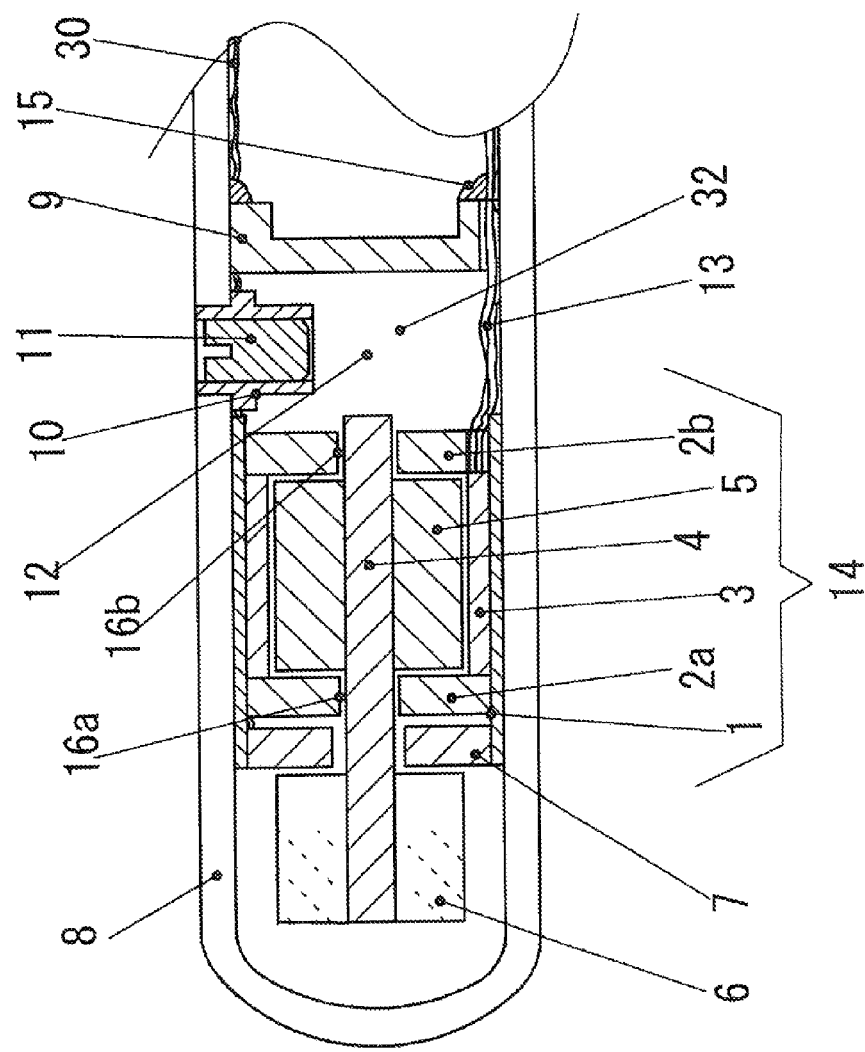
FIG. 1 is a cross sectional view of the ultrasonic endoscopic probe according to a first embodiment of the present invention.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

According to a first feature of the ultrasonic endoscopic probe of the present embodiment, a catheter type ultrasonic endoscopic probe includes a substantially tubular catheter including a cavity formed by partitioning a part of an inner portion of the catheter, the cavity housing a motor including a motor casing, a rotating shaft, and a bearing for the rotating shaft, an ultrasonic transducer mounted to the rotating shaft, and a signal transmission means that transmits or receives a signal to or from the ultrasonic transducer. The cavity further contains an acoustic coupling fluid sealed therein. The bearing includes an inner peripheral surface provided with a plurality of dynamic pressure generating grooves in an axial direction. The bearing and the rotating shaft have a gap allowing the entry of the acoustic coupling fluid.

According to this configuration, when the ultrasonic transducer and the motor are rotated in the acoustic coupling fluid, the acoustic coupling fluid is suctioned into the gap of the bearing provided with the dynamic pressure generating grooves for lubrication. Thus, high accuracy rotation can be executed by preventing the lack of an oil film on the bearing, and operation failure due to the development of foam in the acoustic coupling fluid can be prevented, whereby a high resolution ultrasonic observation image can be obtained.

According to a second feature, the dynamic pressure generating grooves may have a bearing slide surface area ratio (area of grooves/area of bearing slide surface) in a range of 5 to 20%.

According to this configuration, the acoustic coupling fluid can enter the bearing gap in a preferable manner, whereby high bearing rotation accuracy can be achieved, and a high resolution ultrasonic observation image can be obtained.

According to a third feature, the dynamic pressure generating grooves may have a groove depth in a range of 0.5 µm to 2 µm.

According to this configuration, the acoustic coupling fluid can enter the bearing gap in a preferable manner, whereby high bearing rotation accuracy can be achieved and a high resolution ultrasonic observation image can be obtained.

According to a fourth feature, the dynamic pressure generating grooves have a bearing slide surface area ratio (area of grooves/area of bearing slide surface) in a range of 5 to 20 percent; and the dynamic pressure generating grooves have a groove depth in a range of 0.5 µm to 2 µm.

According to this configuration, the acoustic coupling fluid can enter the bearing gap in a preferable manner, whereby high bearing rotation accuracy can be achieved, and a high resolution ultrasonic observation image can be obtained.

According to a fourth feature, the acoustic coupling fluid sealed in the cavity may be a mineral oil or a silicon oil.

According to this configuration, the acoustic coupling fluid can enter the bearing gap in a preferable manner. As a result, the generation of air bubbles in the oil can be prevented, and the interference to an ultrasonic scan by remaining gas can be prevented, whereby a high resolution ultrasonic observation image can be obtained.

According to a fifth feature, the rotating shaft may have a hollow shape with a hollow opening into which a bar-like non-rotating object is inserted. The bar-like object may be configured to be sealed by being fixed in the opening of the seal plate.

According to this configuration, a device using an optical fiber, such as an observation device, can be simultaneously configured in the catheter of the ultrasonic endoscopic probe.

According to a sixth feature, a tubular object may be inserted in a hollow opening of the rotating shaft, the tubular object being fixed in the opening of the seal plate and sealed therein. One of an electric wire, a wire, and an optical fiber may be inserted inside the pipe-like object.

According to this configuration, a tube can be inserted in the catheter of the ultrasonic endoscopic probe. Thus, a multifunctional ultrasonic endoscopic probe can be configured by inserting an endoscopic treatment guide wire or a camera signal line, for example, in the tube.

Preferable embodiments of the present invention will be described with reference to the drawings.

First Embodiment

FIGS. 1 to 6 illustrate a first embodiment of the ultrasonic endoscopic probe according to the present invention.

In FIG. 1 which is a cross sectional view of a tip portion of the ultrasonic endoscopic probe according to the first embodiment of the present invention, there is illustrated a tubular catheter 8 housing a motor 14. The motor 14 includes a motor casing 1 to which bearings 2a and 2b are mounted, the bearings rotatably supporting a rotating shaft 4 to which a rotor magnet 5 is mounted. A motor coil 3 is mounted to the motor casing 1 which is supplied with electric power via an electric wire 13 so as to cause the rotor magnet 5 to generate rotating torque.

To the rotating shaft 4, an ultrasonic transducer 6 is mounted. The ultrasonic transducer 6 is disposed facing a signal transmission means 7 and is mounted in the catheter 8 or the motor casing 1. The signal transmission means 7 herein refers to a multi-channel conductive brush unit or a wireless rotary transformer, for example.

In the catheter 8, a seal plate 9 is mounted, which is sealed by a sealant 15, forming a cavity 32. The motor 14, the ultrasonic transducer 6, and the signal transmission means 7 are disposed in the cavity and hermetically sealed therein. At one portion of the cavity, an inlet 10 is mounted. After an acoustic coupling fluid 12 is injected into the cavity 32 via the inlet 10, the catheter 8 is let stand in a decompressed container for a certain time, and thereafter removed. After the internal air bubbles are discharged, the acoustic coupling fluid 12 is sealed by closing the inlet 10 with a plug 11, thus hermetically sealing the cavity 32.

In the following, the operation and effect of the ultrasonic endoscopic probe according to the present invention will be described.

As electric power is supplied via the electric wire 13, the rotating shaft 4 begins to rotate. Simultaneously, the ultrasonic transducer 6 is fed from the signal transmission means 7, causing the ultrasonic transducer 6 to radiate ultrasonic waves of 10 MHz to 400 MHz. The radiated ultrasonic waves pass through the acoustic coupling fluid 12 and the catheter 8, and irradiate a tested portion of a human body, for example. The ultrasonic waves are changed by the state of cellular tissues and then reflected. The reflected sound waves are received by the ultrasonic transducer 6 and converted into an electric signal. The electric signal is transmitted via the signal transmission means 7 and a signal line 30 to the endoscopic device body. In the present embodiment, the motor 14 is rotated at the rotational speed of 1800 to 3600 rpm, and the ultrasonic waves are radiated throughout the 360° circumference at high speed.

Referring to FIG. 1, after the acoustic coupling fluid 12 is injected into the cavity 32 to the full, the catheter 8 is let stand in a decompressed container at 20,000 pascals or less in absolute terms for about 10 minutes or longer, for example. Then, the catheter 8 is gradually returned to the atmospheric pressure and removed from the decompressed container. After the internal air bubbles are discharged, the inlet 10 is sealed with the plug 11, thus discharging the internal air of the motor 14. In this way, bubbles or remaining gas can be eliminated from the acoustic coupling fluid 12 in the cavity 32. Thus, the residual gas or bubbles can be prevented from interfering with a scan operation by radiation of ultrasonic waves from the ultrasonic transducer 6, and an ultrasonic observation image without any missing signal can be obtained.

Figure 2:
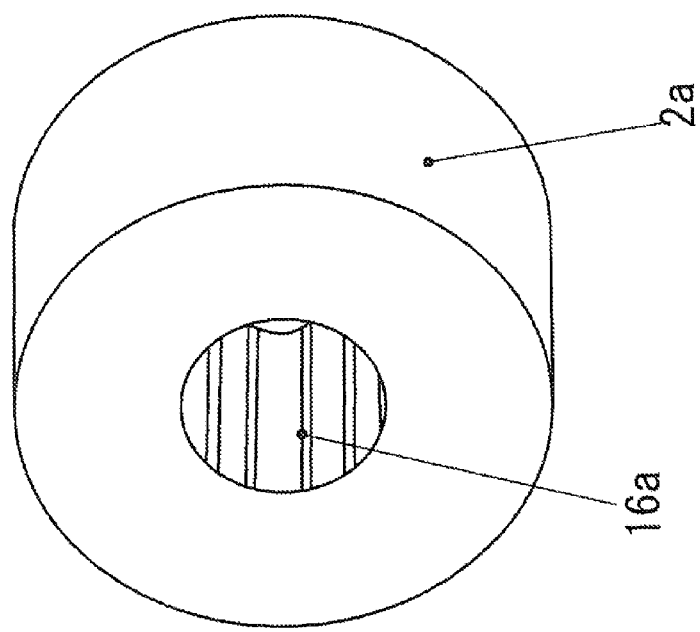
FIG. 2 is a configuration diagram of a dynamic pressure bearing of the ultrasonic endoscopic probe according to the first embodiment of the present invention.

FIG. 2 is a configuration diagram of the bearing 2a with a plurality of straight dynamic pressure generating grooves 16a formed on an inner peripheral surface thereof. According to the present invention, the bearing 2a has an internal diameter dimension in the range of 0.3 mm to 1.2 mm, with a radial gap designed in the range of 1 μm to 3 μm. The number of the dynamic pressure generating grooves 16a is in the range of 4 to 16.

The unique specification of the dynamic pressure generating grooves 16a will be described. According to the present embodiment, in order to ensure equal performance whether the rotation direction of the shaft is in normal or reverse, the dynamic pressure generating grooves 16a are provided in parallel with the shaft (namely, at 90° angle with respect to the direction of rotational flow of the lubrication fluid).

Figure 3:
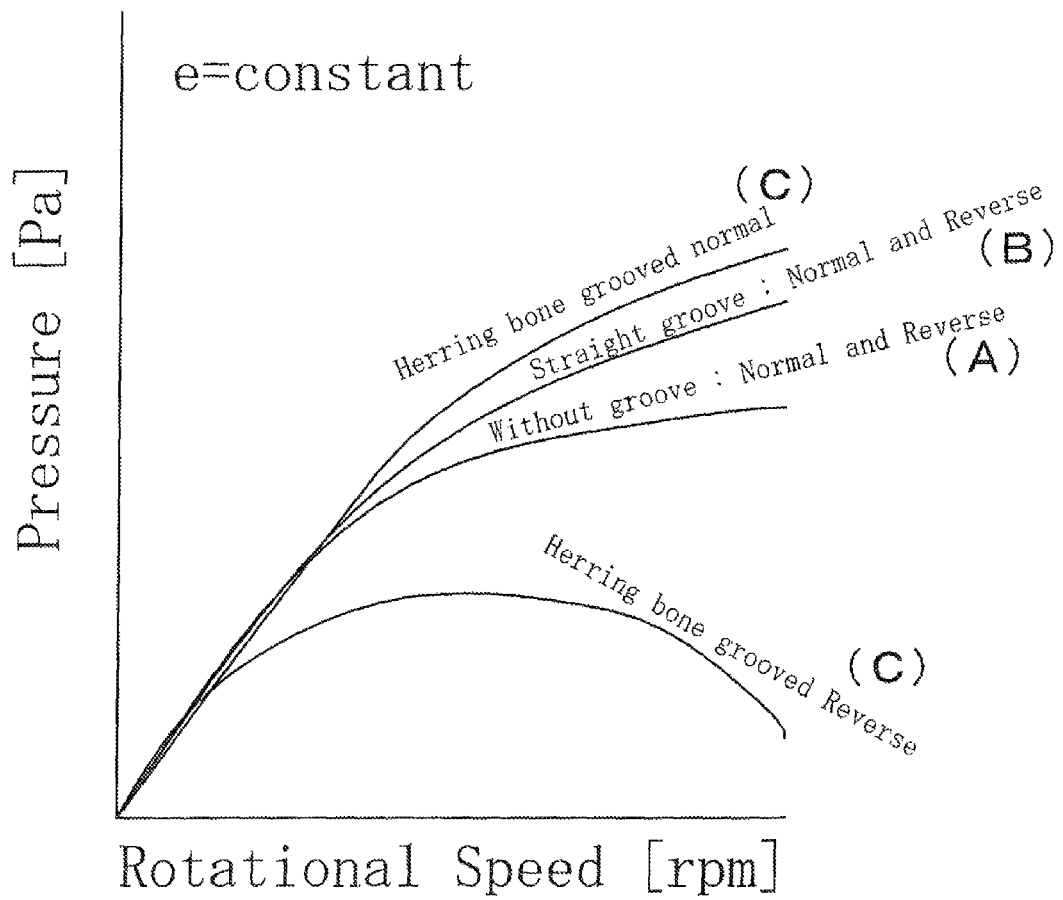
FIG. 3 is a performance characteristics chart of the dynamic pressure bearing of the ultrasonic endoscopic probe according to the first embodiment of the present invention and other bearings.

FIG. 3 illustrates the relationship between the dynamic pressure bearing grooves 16a of the present invention and the pressure (Pa: pascal) generated in the bearing, comparing the pressure values generated at different rotation speeds of a total of three types of bearings, including (A) a normal slide bearing without the dynamic pressure generating grooves; (B) the dynamic pressure bearing having the straight grooves 16a of the present invention; and (C) general herringbone groove dynamic pressure bearings having an angle of about 30° with respect to the flow direction of lubrication fluid. The two types of dynamic pressure bearings have higher generated pressures than the normal slide bearing. However, when the rotation direction is reversed, the performance of the bearing with the straight grooves 16a according to the present invention is such that the acoustic coupling fluid 12 can be more readily suctioned into bearing gaps between the bearings 2a and 2b and the rotating shaft 4 than the herringbone grooved bearing, thus enabling good lubrication and indicating optimum pressure value.

Figure 4:
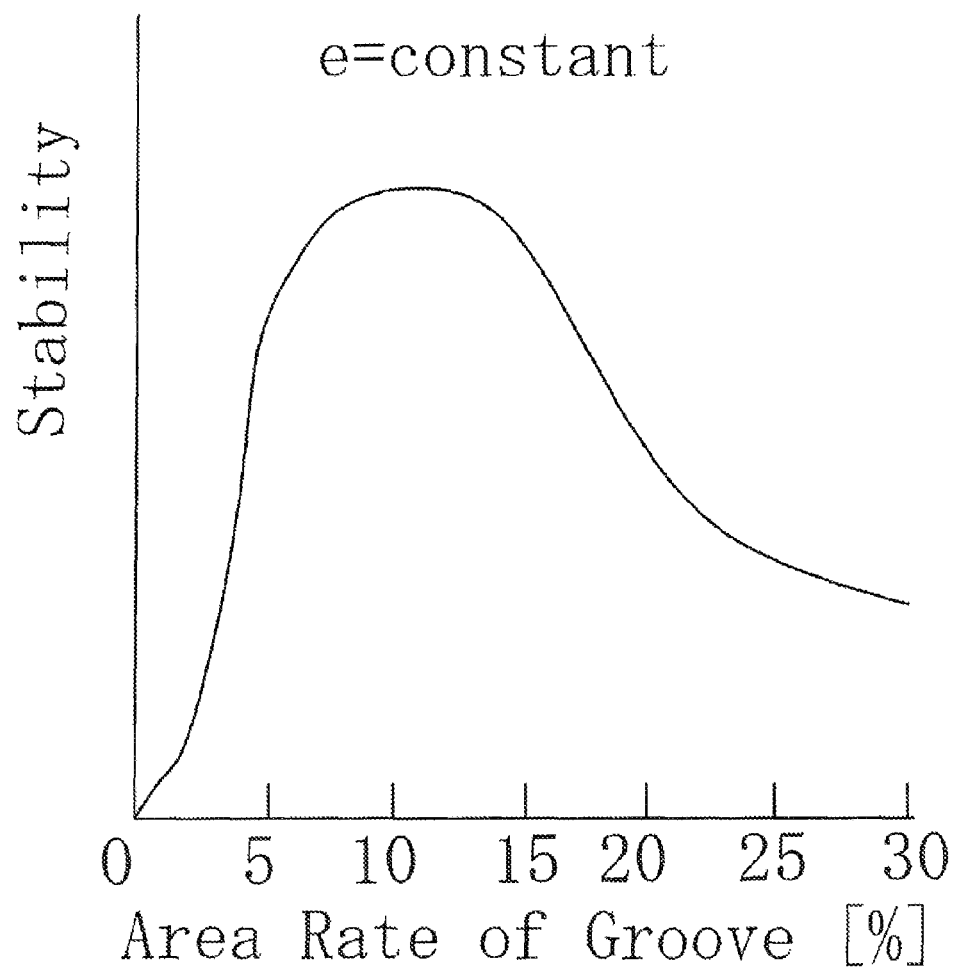
FIG. 4 is a performance characteristics chart of the dynamic pressure bearing of the ultrasonic endoscopic probe according to the first embodiment of the present invention.

FIG. 4 illustrates the rotation stability of the dynamic pressure bearing for the endoscope of the present invention. The rotation stability refers to a state such that the amount of non-repeatable run out, or "half-speed whirl", of the bearing is at a minimum, where there is no contact with the rotation of the bearing, the rotation speed irregularity is at a minimum, and the surrounding acoustic coupling fluid 12 can be readily suctioned into the bearing gap, thus preventing a lack of oil film. In normal dynamic pressure bearings, the dynamic pressure generating grooves 16a have a groove area ratio (area of grooves/area of bearing surface (%)) of about 50% as a general design value. In the dynamic pressure bearing of the present invention, the groove area ratio is designed in the range of 5% to 20%, whereby the acoustic coupling fluid 12 can be guided to the bearing gap in a preferable manner, thus producing a pressure and providing good rotation performance. It has been confirmed that values outside the range of 5% to 20% cause a significant difficulty in the suctioning of the acoustic coupling fluid into the bearing gap, thus adversely affecting performance. In this case, the bearing dimensions, lubrication fluid viscosity, and the eccentricity of the shaft center are those in a certain case. Under conditions such that the eccentricity is extremely large and bearing contact is caused, the influence of the area ratio of the grooves 16a is small. However, under the bearing operation condition where there is good bearing lubrication without extremely large eccentricity, as according to the present embodiment, the area ratio is important.

Figure 5:
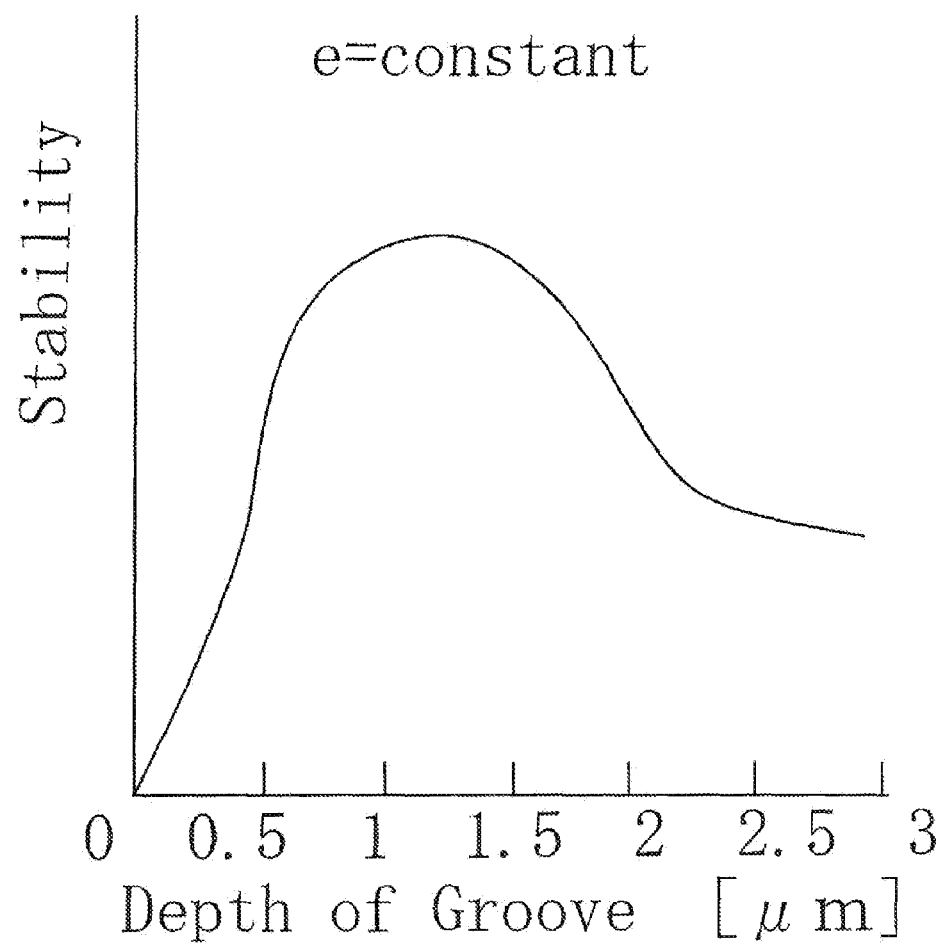
FIG. 5 is a performance characteristics chart of the dynamic pressure bearing of the ultrasonic endoscopic probe according to the first embodiment of the present invention.

FIG. 5 illustrates the relationship between the depth and rotation stability of the dynamic pressure generating grooves 16a of the dynamic pressure bearing of the present invention. In the dynamic pressure bearing of the present invention, when the depth of the dynamic pressure generating grooves 16a is designed in the range of 0.5 μm to 2 μm (microns), preferable rotation performance is obtained. Thus, compared with the normal dynamic pressure bearings with the groove depth of 3 μm or more, best bearing performance is obtained when the depth is significantly small. As regards the groove depth too, it has also been confirmed that in the present invention, values outside the range of 0.5 μm to 2 μm make it significantly difficult to suction the acoustic coupling fluid and adversely affects performance. In this case, too, the bearing dimensions, lubrication fluid viscosity, and the shaft center eccentricity are those in a certain case.

When the design ranges are the appropriate ranges according to the present invention which are different from conventional ranges, as the motor 14 starts to rotate, the dynamic pressure generating grooves 16a operate to collect the acoustic coupling fluid 12 in the cavity 32 into the bearing gap. As a result, a sufficient oil film is formed, allowing the rotating shaft 4 to float together with the ultrasonic transducer 6 and to begin to rotate highly accurately and smoothly in a non-contact manner.

Thus, the bearing 2a allows the rotating shaft 4 to rotate stably while floating and without contacting the bearing 2a, whereby variation in rotation friction torque is reduced and the rotation speed accuracy of the motor 14 is improved. At the same time, because of the effect of the pressure generated by the dynamic pressure generating grooves 16a, the non-repeatable run out of the rotating shaft or "half-speed whirl" is significantly decreased. As a result, the scan accuracy of the ultrasonic transducer 6 and the spatial resolution of the endoscopic device are increased, whereby a good observation image can be obtained.

The type of the acoustic coupling fluid 12 filling the cavity 32 may vary, such as saline solution, pure water, mineral oil, silicon oil, or fluorine oil, as shown in FIG. 6. Among others, saline solution and pure water may cause the problem of corroding the internal ultrasonic transducer 6, the signal transmission means 7 and the like. Fluorine oil has the disadvantage of readily causing bubbles in the oil due to rotation of internal mechanisms such as the motor. Thus, in the ultrasonic endoscopic probe according to the present invention, mineral oil or silicon oil is adopted as the acoustic coupling fluid 12. The viscosity of the oil is selected to be about 25 to 150 (centipoise) at 20° C. in consideration of bubbles prevention and bearing lubrication performance. When other fluids are used, missing dots or image disturbance may be caused in the observation image produced by the ultrasonic endoscopic probe.

The ultrasonic endoscopic probe of FIG. 1 may be inserted into the stomach or the small intestine of the human body, or may be inserted into the vicinity of an affected area during a brain surgery for diagnostic purposes. Thus, the catheter 8 has a diameter of about 3 mm or less with adequate stiffness and flexibility, and is made of material resistant to damages such as surface breakage or pinholes. An exemplary material is fluorine resin.

The characteristic operation and effect of the ultrasonic endoscopic probe illustrated in FIGS. 1 to 6 will be described.

In the ultrasonic diagnostic imaging devices, the most important required performance is high spatial resolution (for example, a target value is 10 μm or less). In the endoscope of the present invention, the ultrasonic transducer 6 is rotated in the improved dynamic pressure generating grooves 16a with the special specification, with the acoustic coupling fluid 12 being suctioned into and filling the bearing gap in a preferable manner. In this way, rotation speed irregularity and oscillation accuracy as well as spatial resolution are improved, while the generation of bubbles in the acoustic coupling fluid 12 is prevented, thus preventing misses in the observation image. Further, the degradation of the acoustic coupling fluid characteristics by a chemical reaction of the lubrication oil and the like in the bearing 2 of the motor 14 of the acoustic coupling fluid 12 can be prevented. Thus, in the ultrasonic endoscopic probe of the present invention, a sufficiently high spatial resolution of 10 μm, for example, can be achieved.

Second Embodiment

A second embodiment of the ultrasonic endoscopic probe according to the present invention will be described with reference to FIG. 7.

Figure 7:
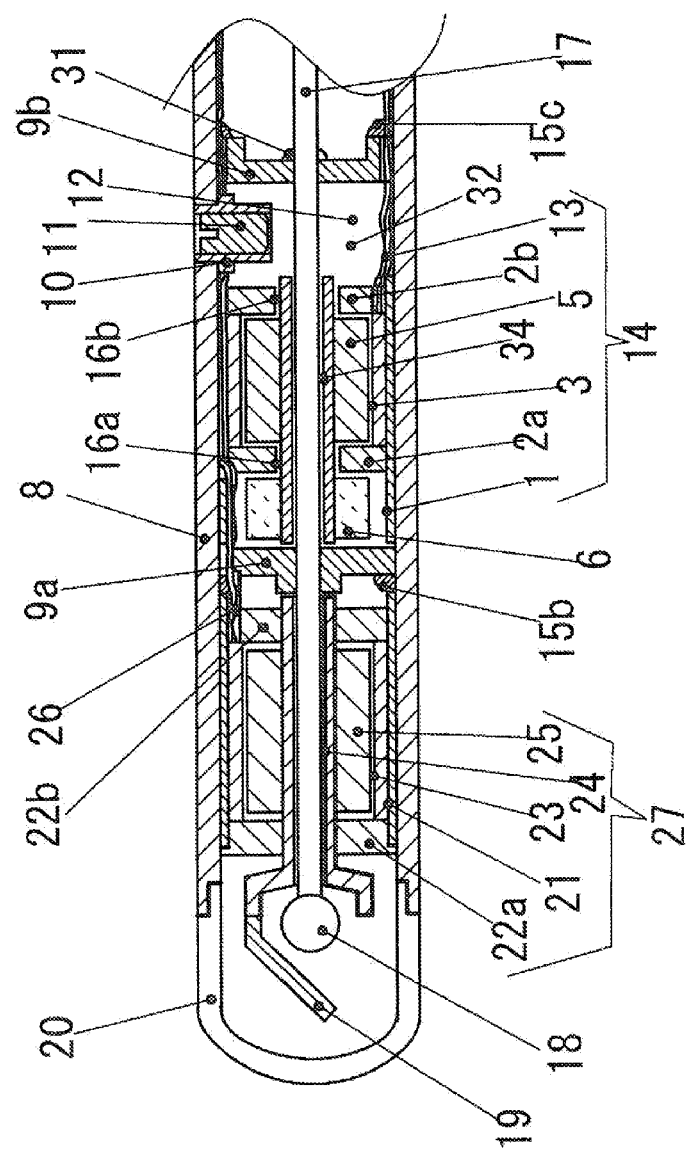
FIG. 7 is a cross sectional view of the ultrasonic endoscopic probe according to a second embodiment of the present invention.

In the ultrasonic endoscopic probe according to the second embodiment illustrated in FIG. 7, the tubular catheter 8 includes the motor 14. The motor 14 houses the motor casing 1 to which the bearings 2a and 2b are mounted, the bearings rotatably supporting a hollow shaft 34 to which the rotor magnet 5 is mounted. The motor coil 3 is mounted to the motor casing 1 which is supplied with electric power via the electric wire 13 so as to cause the rotor magnet 5 to generate rotating torque. To the hollow shaft 34, the ultrasonic transducer 6 is mounted.

A freely bendable optical fiber 17 for guiding a light ray from the rear end side to the tip side of the substantially tubular catheter 8 is inserted in the catheter 8, having a sufficient length, through openings in seal plates 9a and 9b to be fixed therein. At the tip of the optical fiber 17, there is disposed a radiating means 18, such as a ball lens, for condensing a near infrared ray transmitted through the optical fiber 17 and radiating the ray in the tip direction. Also at the tip side of the optical fiber 17, there is mounted a substantially planar rotating mirror 19 which is rotatable by a second motor 27 independently of the optical fiber 17, which is fixed and not rotatable. The rotating mirror 19 is configured to be rotatable so that the near infrared ray can be radiated in any peripheral direction toward a tested specimen of the human body, for example.

The second motor 27 includes a second motor casing 21 in which second bearings 22a and 22b with respective dynamic pressure generating grooves 16a and 16b and a second motor coil 23 are fixed. A second hollow shaft 24 to which a second rotor magnet 25 and the rotating mirror 19 are mounted is rotated. To the second motor coil 23, electric power is supplied via a second electric wire 26.

The seal plates 9a and 9b mounted in the catheter 8 are sealed by sealants 15b and 15c, forming a cavity 32. The motor 14 and the ultrasonic transducer 6 are disposed in the cavity 32 and sealed therein. At one portion of the cavity 32, the inlet 10 is provided. After the acoustic coupling fluid 12 is injected into the cavity 32, the catheter 8 is let stand under decompression for a certain time. Thereafter, the catheter 8 is removed from the decompressed environment, and the inlet 10 is closed with the plug 11 after the internal air bubbles are discharged, whereby the cavity 32 is hermetically sealed.

In FIG. 7, in the vicinity of the outer periphery of the rotating mirror 19 from which a light ray is radiated, a light transmitting portion 20 capable of light ray transmission is mounted to the catheter 8. The light transmitting portion 20 is made from a transparent resin or the like, and is provided with a coating and the like for decreasing surface reflection while increasing light ray transmittance as needed.

In the following, the operation and effect of the ultrasonic endoscopic probe according to the second embodiment of the present invention will be described.

As electric power is supplied via the electric wire 13, the hollow shaft 34 starts to rotate, while simultaneously ultrasonic waves are radiated from the ultrasonic transducer 6. The radiated ultrasonic waves pass through the acoustic coupling fluid 12 and the catheter 8, and irradiate a tested portion of a human body, for example. Then, the ultrasonic waves are changed by the state of cellular tissues and reflected. The reflected sound waves are received by the ultrasonic transducer 6 and converted into an electric signal. The electric signal is sent to the endoscopic device body where the signal is converted into an observation image for display.

When the second motor 27 is energized via the second electric wire 26, the second hollow shaft 24 rotates the rotating mirror 19, whereby near infrared rays are radiated throughout the 360° circumference. The near infrared rays radiated toward the tested specimen of the human body impinge on an affected area of the human body, for example. The impinging rays are changed by the state of the affected area and then reflected. The reflected light is successively passed through the rotating mirror 19, the ball lens 18, and the optical fiber 17 and eventually sent to the endoscope body portion, where the light is converted into a tomography image for display by an optical coherence tomographic observation device utilizing the coherence of the light.

The hollow shaft 34 and the second hollow shaft 24 shown in FIG. 7 have an opening diameter of 0.2 mm to 0.8 mm. The hollow shaft 34 and the second hollow shaft 24 are made of a metal, such as stainless steel, or a ceramics material, and molded into a hollow by drawing a molten metal using a die or by extruding pre-firing ceramics using a die. After a hardening process, the outer periphery surface is finished by polishing process and the like.

Third Embodiment

A third embodiment of the ultrasonic endoscopic probe of the present invention will be described with reference to FIG. 8.

Figure 8:
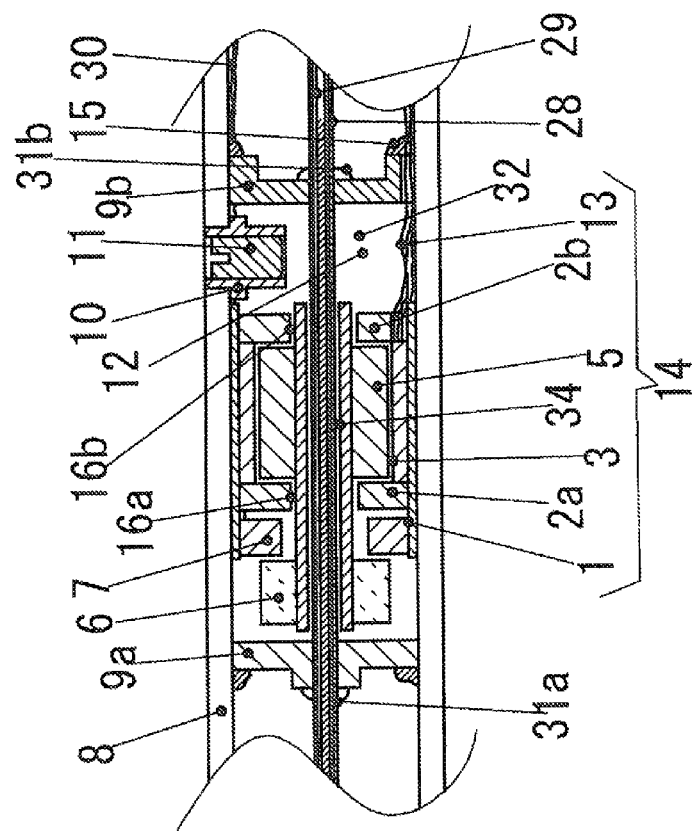
FIG. 8 is a cross sectional view of the ultrasonic endoscopic probe according to a third embodiment of the present invention.

In the third embodiment of the ultrasonic endoscopic probe illustrated in FIG. 8, the bearings 2a and 2b with the dynamic pressure generating grooves 16a and 16b are mounted to the motor casing 1, thus the bearings rotatably supporting the rotating hollow shaft 34 to which the rotor magnet 5 is mounted.

As illustrated in FIG. 8, the catheter 8 includes the motor 14. The motor 14 includes the motor casing 1 to which the motor coil 3 is mounted. The motor coil 3 is supplied with electric power via the electric wire 13, whereby the rotor magnet 5 generates rotating torque. To the hollow shaft 34, the ultrasonic transducer 6 is mounted. The signal transmission means 7 is disposed facing the ultrasonic transducer 6 in the motor casing 1 or the catheter 8.

In the rotating hollow shaft 34, a fixed tube 28 is inserted. The fixed tube 28 is fixedly inserted in the openings of the seal plates 9a and 9b. In the fixed tube 28, a guide wire 29 and the like for performing treatment of an affected area of a human body at the tip portion of the endoscope is freely inserted. A signal line or an optical fiber may also be freely inserted in the fixed tube 28.

The seal plates 9a and 9b are sealed by the sealant 15 and sealants 31a and 31b, forming the cavity 32. The motor 14 and the ultrasonic transducer 6 are disposed in the cavity 32 and hermetically sealed therein. At one portion of the cavity 32, the inlet 10 is provided. After the acoustic coupling fluid 12 is injected into the cavity 32, the catheter 8 is let stand under decompression for a certain time and then removed. After the internal air bubbles are discharged, the inlet 10 is closed with the plug 11, whereby the cavity 32 is hermetically sealed.

In the following, the operation and effect of the ultrasonic endoscopic probe according to the third embodiment of the present invention will be described.

When electric power is supplied via the electric wire 13, the hollow shaft 34 begins to rotate while simultaneously the ultrasonic transducer 6 is fed from the signal transmission means 7, whereby the ultrasonic transducer 6 radiates high frequency ultrasonic waves.

The radiated ultrasonic waves pass through the acoustic coupling fluid 12 and the catheter 8 and irradiate the tested portion of a human body, for example. From the tested specimen, the ultrasonic waves that have been changed by the state of the cellular tissues are reflected. The reflected sound waves are received by the ultrasonic transducer 6 and converted into an electric signal. The electric signal is sent via the signal transmission means 7 and the signal line 30 to the endoscopic device body, where a corresponding tomography image is displayed.

According to this configuration, a tube can be disposed penetrating the catheter of the ultrasonic endoscopic probe. Thus, a multi-functional ultrasonic endoscopic probe can be configured by passing an endoscopic treatment guide wire, a camera signal line and the like through the tube.

According to the present invention, in an ultrasonic endoscopic probe in which an ultrasonic transducer is rotated together with a motor in an acoustic coupling fluid, misses in an ultrasonic observation image due to air bubbles produced by the mixing of the acoustic coupling fluid with bearing oil can be prevented. The bearing gap can be filled with the acoustic coupling fluid in a preferable manner. Thus, the lack of an oil film or rotation irregularity can be prevented, and high accuracy rotation of the bearing can be ensured, whereby a high-resolution observation image can be obtained.

The ultrasonic endoscopic probe according to the present invention enables the acquisition of a clear ultrasonic analysis image having high spatial resolution. Thus, the ultrasonic endoscopic probe may be effectively utilized in the medical field, in particular, for diagnosis or treatment of fine lesions. The ultrasonic endoscopic probe may also be applied to devices other than medical endoscopic devices, such as industrial diagnostic devices.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A catheter type ultrasonic endoscopic probe comprising a catheter including a tubular portion and a cavity formed by partitioning a part of an inner portion of the catheter,
   the cavity housing a motor including a motor casing, a rotating shaft, and a bearing for the rotating shaft, an ultrasonic transducer mounted to the rotating shaft, and a signal transmitter that transmits or receives a signal to or from the ultrasonic transducer,
   wherein:
   the cavity further contains an acoustic coupling fluid sealed therein;
   the bearing includes an inner peripheral surface provided with a plurality of dynamic pressure generating grooves in an axial direction of the rotating shaft;
   a gap for allowing penetration by the acoustic coupling fluid is provided between the bearing and the rotating shaft in a radial direction of the rotating shaft; and
   the dynamic pressure generating grooves have a bearing slide surface area ratio (area of grooves/area of bearing slide surface) in a range of 5 to 20 percent.

2. The ultrasonic endoscopic probe according to claim 1, wherein the acoustic coupling fluid sealed in the cavity is a mineral oil or a silicon oil.

3. The ultrasonic endoscopic probe according to claim 1, wherein the rotating shaft has a hollow shape with a hollow opening into which a bar-like non-rotating object is inserted.

4. The ultrasonic endoscopic probe according to claim 1, wherein:
   the rotating shaft has a hollow shape with a hollow opening into which a non-rotating tubular object is inserted; and
   one of an electric wire, a wire, and an optical fiber is inserted in the non-rotating tubular object.

5. A catheter type ultrasonic endoscopic probe, comprising a catheter including a tubular portion and a cavity formed by partitioning a part of an inner portion of the catheter, the cavity housing a motor including a motor casing, a rotating shaft, and a bearing for the rotating shaft, an ultrasonic transducer mounted to the rotating shaft, and a signal transmitter that transmits or receives a signal to or from the ultrasonic transducer, wherein:

the cavity further contains an acoustic coupling fluid sealed therein;

the bearing includes an inner peripheral surface provided with a plurality of dynamic pressure generating grooves in an axial direction of the rotating shaft;

a gap for allowing penetration by the acoustic coupling fluid is provided between the bearing and the rotating shaft in a radial direction of the rotating shaft; and the dynamic pressure generating grooves have a groove depth in a range of 0.5 µm to 2 µm.

6. A catheter type ultrasonic endoscopic probe, comprising a catheter including a tubular portion and a cavity formed by partitioning a part of an inner portion of the catheter, the cavity housing a motor including a motor casing, a rotating shaft, and a bearing for the rotating shaft, an ultrasonic transducer mounted to the rotating shaft, and a signal transmitter that transmits or receives a signal to or from the ultrasonic transducer, wherein:

the cavity further contains an acoustic coupling fluid sealed therein;

the bearing includes an inner peripheral surface provided with a plurality of dynamic pressure generating grooves in an axial direction of the rotating shaft;

a gap for allowing penetration by the acoustic coupling fluid is provided between the bearing and the rotating shaft in a radial direction of the rotating shaft;

the dynamic pressure generating grooves have a bearing slide surface area ratio (area of grooves/area of bearing slide surface) in a range of 5 to 20 percent; and the dynamic pressure generating grooves have a groove depth in a range of 0.5 µm to 2 µm.

\* \* \* \* \*